(12) United States Patent
Khachik

(10) Patent No.: US 6,262,284 B1
(45) Date of Patent: Jul. 17, 2001

(54) PROCESS FOR EXTRACTION AND PURIFICATION OF LUTEIN, ZEAXANTHIN AND RARE CAROTENOIDS FROM MARIGOLD FLOWERS AND PLANTS

(75) Inventor: Frederick Khachik, Beltsville, MD (US)

(73) Assignee: University of Maryland, College Park, MD (US)

( * ) Notice: Subject to any disclaimer, the term of this patent is extended or adjusted under 35 U.S.C. 154(b) by 0 days.

(21) Appl. No.: 09/529,815

(22) PCT Filed: Oct. 21, 1998

(86) PCT No.: PCT/US98/22229

§ 371 Date: Apr. 20, 2000

§ 102(e) Date: Apr. 20, 2000

(87) PCT Pub. No.: WO99/20587

PCT Pub. Date: Apr. 29, 1999

(51) Int. Cl.[7] .................................................. C07C 1/07
(52) U.S. Cl. ................ 554/14; 554/13; 554/19; 554/20; 568/830
(58) Field of Search .................... 554/13, 14, 20, 554/19; 568/534

(56) References Cited

U.S. PATENT DOCUMENTS

| | | |
|---|---|---|
| 4,048,203 | 9/1977 | Philip . |
| 5,382,714 | 1/1995 | Khachik . |
| 5,648,564 | 7/1997 | Ausich et al. . |

OTHER PUBLICATIONS

J.K. Tycakowski, et al., "Preparation of Purified Lutein and its Diesters . . . Marigold" in Poultry Science, vol. 70, No. 3 (Mar. 1991), pp. 651–654.

F. Khachik, et al., "Isolation, Structural Elucidation and Partial Synthesis of Lutein Dehydration Products . . . Plasma" in Journal of Chromatography B, vol. 670 (1995), pp. 219–233.

F. Khachik, et al., "Separation, Identification, and Quantification of Carotenoids in Fruits . . . Chromatography" in Pure & Appl. Chem., vol. 63, No. 1 (1991), pp. 71–80.

F. Khachik, et al., "Lutein, Lycopene, and their Oxidative Metabolites . . . Cancer" in Journal of Cellular Biochemistry, Suppl. 22 (1995), pp. 236–246.

F. Khachik, et al., "Identification of Lutein and Zeaxanthin Oxidation Products . . . Retinas" in Investigative Ophthalmology & Visual Science, vol. 38, No. 9 (Aug. 1997), pp. 1802–1811.

F. Khachik, et al., "Isolation and Structural Elucidation of . . . Human Plazma" in Journal of Chromatography, vol. 592 (1999), pp. 153–166.

F. Khachik, et al., "Identification, Quantification, and Relative Concentration . . . Serum" in Analytical Chemistry, vol. 69, No. 10 (May 1997), pp. 1873–1881.

F. Khachik, et al., "Separation, Identification, and Quantification of the Major Carotenoids . . . Chromatography" in Journal of Agricultural & Food Chemistry, vol. 37, No. 6 (1989), pp. 1465–1473.

F. Khachik, et al., "Decapreno–B–Carotene Chromatography" in Journal of Chromatography, vol. 346 (1985), pp. 237–246.

F. Khachik, et al., "Separation and Identification of Carotenoids . . . Human Plasma" in Analytical Chemistry, vol. 64, No. 18 (Sep. 1992), pp. 2111–2122.

F. Khachik, et al., "Application of a C–45–B–Carotene . . . Chromatography" in Journal of Agricultural & Food Chemisry, vol. 35, No. 5 (1987), pp. 732–738.

F. Khachik, et al., "Separation and Identification of Carotenoids . . . Esters by HPLC" in Journal of Agricultural & Food Chemistry, vol. 36, No. 5 (1988), pp. 929–937.

F. Khachik, et al., "Effect of Food Preparation of Qualitative . . . Vegetables" in Journal of Agricultural & Food Chemistry, vol. 40, No. 3 (1992), pp. 390–398.

F. Khachik, et al., "Separation and Quantitation of Carotenoids in Foods" in Methods of Enzymology, vol. 213 (1992), pp. 347–359.

F. Khachik, et al., "Carotenoid Content of Thermally Processed . . . Products" in Journal Agricultural & Food Chemistry vol. 43, No. 3 (1995), pp. 579–586.

*Primary Examiner*—Deborah D. Carr
(74) *Attorney, Agent, or Firm*—Dykema Gossett PLLC

(57) ABSTRACT

A process for simultaneously extracting, saponifying, and isolating lutein and zeaxanthin, and a mixture of several rare carotenoids in high purity from plants without the use of harmful organic solvents. Lutein crystals containing 5% zeaxanthin were obtained from the dried petals of Marigold flowers *Tagete erecla* while zeaxanthin was isolated and purified from the berries of *Lycium Chinese Mill* (LCM berries). Similarly, this process has been employed to isolate and purify a mixture of lutein, beta-carotene, neoxanthin, violaxanthin, and lutein epoxide from green plants, preferably, kale, collard green, and spinach. These plants, to a lesser extent, also serve as a source of several rare carotenoids such as alpha-cryptoxanthin (Marigolds) and beta-cryptoxanthin (LCM berries). The purified carotenoids isolated by this process are free from impurities and serve as a safe source of nutritional supplement for human consumption as well as providing a suitable and effective color additive for human foods.

22 Claims, No Drawings

PROCESS FOR EXTRACTION AND PURIFICATION OF LUTEIN, ZEAXANTHIN AND RARE CAROTENOIDS FROM MARIGOLD FLOWERS AND PLANTS

This application is a 371 of PCT/US 98/2229 filed Oct. 21, 1998.

1. FIELD OF THE INVENTION

A simultaneous process for extraction, isolation, and purification of lutein, zeaxanthin, and several rare carotenoids from Marigold flowers, Lycium Chinese Mill, and green plants.

2. BACKGROUND OF THE INVENTION

Carotenoids are amongst the most widespread of the naturally occurring groups of pigments and are found in all families of the plant and animal kingdoms. To date, as many as seven hundred carotenoids have been isolated from various sources and their chemical structures have been characterized. Numerous epidemiological studies in various populations have shown that consumption of substantial amounts of fruits and vegetables rich in carotenoids reduces the risk of acquiring several types of cancers. As a result, for nearly two decades, scientists have been focussing most of their attention on investigating the protective effect of beta-carotene in prevention of cancer, cardiovascular and eye diseases. This is despite the fact that beta-carotene is only one of the prominent carotenoids found in fruits and vegetables whose consumption has been associated with health benefits in humans. The reasons for such an intense focus can be attributed to the pro-vitamin A activity of beta-carotene and the lack of commercial availability of other prominent food carotenoids.

During the past decade, the author and coworkers have isolated, identified, and quantified carotenoids from fruits and vegetables commonly consumed in the U.S. These studies have revealed that as many as 40 to 50 carotenoids may be available from the diet and absorbed, metabolized, or utilized by the human body (Khachik et al. 1991, Pure Appl. Chem., 63: 71–80). However, among these, only 13 carotenoids and 12 of their stereoisomers are routinely found in human serum and milk (Khachik et al. 1997, Anal. Chem. 69:1873–1881). In addition, there are 8 carotenoid metabolites and one stereoisomer in human serum or plasma which result from a series of oxidation-reduction reactions of three dietary carotenoids, namely, lutein, zeaxanthin, and lycopene. These metabolites were first isolated and characterized by Khachik et al. (1992, Anal. Chem. 64: 2111–2122). In another study, the ingestion of purified supplements of dietary (3R,3'R,6'R)-lutein and (3R,3'R)-zeaxanthin was shown to not only result in an increase in the blood levels of these compounds in humans but also increased the concentration of their oxidative metabolites in plasma (Khachik et al. 1995, J. Cellular Biochem. 22:236–246). These findings, for the first time, provided preliminary evidence for the long standing hypothesis that carotenoids may function as anti-oxidants in disease prevention. In addition, these results also established the importance of non-vitamin A active dietary carotenoids, particularly, lutein, zeaxanthin, and lycopene.

In 1985 and 1993, Bone et al. (1985, Vision Res. 25: 1531–1535; 1993, Invest. Ophthalmol. Vis. Sci. 34: 2033–2040) elegantly demonstrated that the human macular pigment is a combination of lutein and zeaxanthin and speculated that these dietary carotenoids may play an important role in the prevention of an eye disease, namely, Age-Related Macular Degeneration (ARMD). This was later confirmed in a case-controlled epidemiological study in which the high consumption of fruits and vegetables, rich specifically in lutein and zeaxanthin, was correlated to a 43% lower risk of ARMD (Seddon et al. 1994, J. Am. Med. Assoc. 272: 1413–1420). More recently, in addition to lutein and zeaxanthin, the author and his co-workers reported on the isolation and identification of one major and several minor oxidation products of lutein and zeaxanthin in human and monkey retinas (Khachik et al. 1997, J. Invest. Ophthalmol. Vis. Sci. 38:1802–1811). The authors then proposed a metabolic pathways for these compounds which may play an important role in the prevention of ARMD. Therefore the commercial production of the purified forms of dietary carotenoids in general, particularly lutein and zeaxanthin, is of great importance. These carotenoids may be used, individually or in combination, as nutritional supplements and food colorants as well as in clinical trials where their potential health benefits in the prevention of ARMD and cancer can be investigated.

Although lutein and zeaxanthin may be obtained from certain fruits and vegetables, the isolation of lutein from extracts of marigold flowers and zeaxanthin from berries of *Lycium Chinese Mill* (LCM berries) proves to be most economical. In Marigold flowers lutein is the major carotenoid and is normally accompanied by about 3–6% zeaxanthin; in LCM berries zeaxanthin is the major carotenoid and is completely free from lutein. In both of these plants, lutein and zeaxanthin are esterified with fatty acids such as lauric, myristic, and palmitic acids. The purification of lutein fatty acid esters from marigold flowers was patented by Philip in 1977 (U.S. Pat. No. 4,048,203). However, dietary carotenol fatty acid esters, in general, have not been detected in human plasma or serum. Therefore, upon ingestion of purified lutein fatty acid esters by humans, these compounds partially undergo hydrolysis in the presence of pancreatic secretions in the small intestine to regenerate free lutein which is then absorbed [Khachik et al. Pure & Appl. Chem., 63(1): 71–80, 1991]. Since the most abundant dietary form of lutein is not its esterified form, a commercial process that could provide lutein free from fatty acids was needed.

A method for the purification of free lutein from extracts of marigolds was first reported in 1991 [Tyzkowski and Hamilton, Poultry Sci., 70(3): 651–654, 1991]. However because this method was extremely time-consuming, used harmful organic solvents, and produced poor yields, it could not be implemented commercially.

In view of the important biological activity of lutein and zeaxanthin, the author developed a process for isolation, purification, and recrystallization of lutein from saponified Marigold oleoresin which was patented in 1995 (Khachik, U.S. Pat. No. 5,382,714). The saponified Marigold oleoresin was obtained from Kemin Industries (Des Moines, Iowa) and is normally prepared from extraction of dried Marigold petals with n-hexane, followed by saponification and solvent evaporation. To date, this process is the only available method for isolation and purification of lutein (containing 3–6% zeaxanthin) from Marigolds in purities greater than 97%. Recently, another process for the isolation of lutein from a saponified Marigold oleoresin has been reported wherein lutien can be obtained in 70–85% purity (U.S. Pat. No. 5,648,564, 1997). This process employs propylene glycol (40.9% weight percent) and an aqueous alkali (18.2% weight percent) to saponify a hexane extract of dried Marigold petals (marigold oleoresin, 40.9% weight percent) containing lutein esters at 70° C. in 10 hours.

There are several major disadvantages with this process; these are discussed as follows. The Marigold oleoresin is prepared by extraction of dried marigold petals in boiling n-hexane for extended periods of time. Since lutein/zeaxanthin, and carotenoids in general, are sensitive to heat treatment, this procedure can result in degradation or isomerization of these compounds. Furthermore, according to the Food and Drug administration's (FDA) Federal Register Documents, Code of Federal Regulations & Food, Drug, and Cosmetic act, n-hexane is considered among the solvents whose levels in foods and pharmaceutical products should be limited. The classification of organic solvents by the FDA will be described later in this text.

In the next step of this process, the hydrolysis of lutein and zeaxanthin esters in the marigold oleoresin is conducted in an aqueous solution in the presence of alcohol and propylene glycol in which the fatty acid esters of lutein and zeaxanthin have very low solubility. As a result, this process requires high temperatures of up to 70° C. and 10 hours to complete the saponification. This can once again result in the degradation and isomerization of lutein and zeaxanthin.

Due to the high viscosity of propylene glycol, during handling and several purification steps, the saponified product is additionally subjected to high temperatures ranging from 70 to 85° C. This un-necessary exposure to heat in the presence of air can result in oxidative degradation of lutein and zeaxanthin and formation of a number of side products.

In summary, the above patented process (U.S. Pat. No. 5,648,564) employs extraction and saponification of Marigolds in two separate steps which are then followed by several purification steps. According to the authors, when the extraction and saponification steps were combined to simplify the procedure, the result was a 64.7% reduction in the yield of lutein in comparison to the two-step extraction and saponification processes described above. Overall, these procedures are quite time-consuming, are carried out under harsh conditions, and produce lutein in only 70–85% purity.

The earlier patent by the inventor (Khachik, U.S. Pat. No. 5,382,714) generally has two major disadvantages. This process also uses n-hexane as the extracting solvent and, at the last purification step, it employs dichloromethane and n-hexane as the recrystallization solvents to obtain lutein containing 3–6% zeaxanthin in purities of 97% or greater. Since according to the FDA, the use of dichloromethane and hexane in drug and food products should be limited, the lutein purified by these solvents, should be thoroughly dried under high vacuum to remove residual solvents.

The process described here provides a convenient and economical route to lutein, zeaxanthin, and several minor carotenoids by employing a simultaneous extraction and saponification procedure at room temperature for only a few hours. Most importantly, this process addresses all the disadvantages and concerns with regard to all of the previously patented procedures described above. As a result, the lutein (from Marigolds) and zeaxanthin (from LCM berries) obtained by this process are in purity of 97% or greater and are therefore suitable for human consumption. This extraction and purification process has also been successfully employed for isolation of lutein and several minor carotenoids from green plants which serve as an alternative source for commercial production of lutein.

BRIEF SUMMARY OF THE INVENTION

This invention employs a simultaneous extraction and hydrolysis (saponification) procedure for isolation and purification of lutein, zeaxanthin, and several rare carotenoids from Marigold flowers, LCM berries, and green plants. The plants are mixed with tetrahydrofuran (THF) and sufficient amounts of ethanol or methanol (preferably food grade ethanol) with the addition of either 5% or 10% potassium or sodium hydroxide to maintain the pH at 12 and the mixture is homogenized at room temperature for 1 to 2 hours. This process not only extracts carotenoids from plants under mild conditions, within a few hours, but it simultaneously hydrolyses the fatty acid esters of major dihydroxycarotenoids such as lutein and zeaxanthin as well as monohydroxycarotenoids such as alpha-cryptoxanthin and beta-cryptoxanthin which are present in minute quantities. As a result, the free and un-esterified forms of these hydroxycarotenoids are regenerated.

In the case of green plants, in which lutein is present in its free form, the simultaneous extraction and saponification results in the conversion of chlorophylls to their water soluble derivatives and allows the removal of these compounds from lutein, beta-carotene, and other carotenoids. In the next step, the mixture is filtered off, the solvents (THF and alcohol) are evaporated, and the residue is washed with water until the pH of the aqueous wash is neutral (pH=7.0). This treatment removes the salts of fatty acid esters, the base (potassium or sodium hydroxide), and the water soluble plant components. After centrifugation, depending on the plant source, the resulting crystals of lutein or zeaxanthin are approximately 70% pure and contain minor quantities of other carotenoids. In the final purification step, lutein or zeaxanthin are dissolved in minimum amount of THF, and water is added until the solution becomes cloudy; at this point the recrystalliztion of these compounds takes place. The mixture is then centrifuged and the solid crystals are washed with water or alcohol to remove the THF. After drying under high vacuum, the crystalline lutein or zeaxanthin are obtained in purities of 97% or greater.

Alternatively, 70% lutein or zeaxanthin may be purified by passing a solution of these compounds in THF and water through a column packed with n-silica gel. After collection of the fraction containing lutein or zeaxanthin (greater than 97% purity), the THF is evaporated and the residue is washed with water or alcohol and dried as described above. As separate fractions, several rare carotenoids such as alpha-cryptoxanthin and beta-cryptoxanthin (Marigolds and LCM berries) as well as a mixture of lutein, beta-carotene, neoxanthin, violaxanthin, and lutein epoxide (from greens) are also obtained in high purity.

The processes described above is a convenient and commercially viable method for extraction and isolation of lutein and zeaxanthin from plant sources in which these compounds are esterified with fatty acids. Similarly this method can be applied to green plants where the presence of chlorophylls complicate the isolation of the un-esterified lutein. In addition to purifying lutein and zeaxanthin to 97% or greater, this process also allows the isolation of several rare carotenoids which are not commercially available. The production of carotenoids according to this process can be conducted under controlled and mild conditions at room temperature or below 40° C. to avoid the isomerization and degradation of these heat-sensitive compounds. The only organic solvent used is THF which, due to its solubility, can be easily removed by washing with water and/or alcohol. Consequently, the carotenoids produced according to these procedures can be safely used as nutritional supplements or food coloring additives.

DETAILED DESCRIPTION OF THE INVENTION

Nomenclature

For convenience, the trivial rather than the correct systematic names of carotenoids have been used throughout this text. The chemical structures of lutein [(3R,3'R,6'R)-lutein], zeaxanthin [(3R,3'R)-zeaxanthin], alpha-cryptoxanthin [(3R,6'R)-alpha-cryptoxanthin], and beta-cryptoxanthin [3R-beta-cryptoxanthin], isolated from Marigold flowers (*Tagete erecta*) and berries of *Lycium Chinese Mill*, have been established to be identical with the dietary forms of these compounds found in most fruits and vegetables. The terms all-E and Z isomers of carotenoids refer to all-trans and cis isomers of these compounds. For in-chain geometrical isomers of carotenoids, the terms all-trans and cis, which have been used with the old nomenclature, are no longer appropriate. If not specified, the terms lutein or zeaxanthin refer to the most common geometrical forms (all-E or all-trans) of these carotenoids in plants. The use of the term "lutein esters" or "zeaxanthin esters" refers to either mono- or di- esters without limitation.

The present invention applies a simultaneous extraction and saponification process to three generally different plants sources for isolation of lutein and zeaxanthin; these are: dried petals of Marigolds (*Tagete erecta*), LCM berries (*Lycium Chinese Mill*), and several green vegetables such as Kale (Brassica oleracia, var. acephala), Spinach (*Spinacia oleracia*), and Collard green (*Brassica oleracia*, var. Champion). These plant sources of carotenoids are described as follows.

The dried petals of marigold flowers, are harvested and prepared in Central America and are imported into the U.S. Flowers are hand-picked and ensiled to preserve them until they can be economically dried. The marigold blossoms are then placed in a freeze drying apparatus and are dehydrated under controlled conditions. After dehydration, the flowers are put through a series of air separators and mechanical separators where the petals are separated from any other materials and converted to a homogenous Marigold meal. The carotenoids in Marigold meal are esterified with fatty acids such as lauric, myristic, and palmitic acid, however, upon hydrolysis the parent hydroxycarotenoids are regenerated. As shown in a previous patent by the author (Khachik, 1995, U.S. Pat. No. 5,382,714, herein incorporated by reference), the major hydroxycarotenoid in Marigold is lutein which is normally accompanied by 3–6% of its isomeric compound, zeaxanthin.

LCM berries are normally grown in China and can be obtained from most of the Chinese supermarkets across the U.S. However, a variety of this fruit is also currently grown on a commercial scale by Rehnborg Center for Nutrition in Lakeview, Calif. For the first time in 1995, the author isolated several grams of zeaxanthin from LCM berries for a human supplementation study and demonstrated that this plant is an excellent source of zeaxanthin (Khachik et al., J. Cellular Biochem. 1995, 22:236–246). However, the details of the isolation and purification of zeaxanthin was not published. Zeaxanthin in LCM berries is mostly esterified with palmitic acid and only trace amounts of this compound is esterified with lauric and myristic acids. LCM berries do not contain any measurable amount of lutein but several other carotenoids such as alpha-cryptoxanthin, beta-cryptoxanthin, and beta-carotene are present in this fruit in minute quantities. For the present study, large quantities of the berries were purchased from a local Chinese supermarket.

In a 1986 publication by the author it has been shown that greens are also a good source of lutein and beta-carotene as well as several rare carotenoids such as neoxanthin, violaxanthin, and lutein epoxide (Ehachik et al. J. Agric. Food Chem., 1986, 34: 603–616). Furthermore, the analysis of several green vegetables indicated that the higher the levels of chlorophylls, the higher were the levels of carotenoids. Although in greens, lutein is not esterified and is present in its free form, simultaneous extraction and saponification by the present process converts the chlorophylls to their water-soluble derivatives and allows the isolation and purification of carotenoids. No measurable amount of zeaxanthin can normally be found in green plants. For the present invention, Kale, Spinach, and Collard green were purchased from a local supermarket. These vegetables were selected due to their relatively high lutein content in compare to other common green vegetables. As shown by the author previously, in green plants the general profile of carotenoids are same and the only variations are in concentrations of individual carotenoids. Therefore, the present process can be similarly applied to other dark green plants which may also serve as an economically viable source for isolation of lutein.

In the present invention, the choice of tetrahydrofuran (THF) as the extracting solvent was based on a guideline set by the Department of Health and Human Services, Food and Drug Administration (FDA) in Docket No. 97D-0148 published in Federal Register: May 2, 1997 (volume 62, Number 85, pages 24301–24309). The draft guideline entitled "Impurities: Residual Solvents" and was prepared under the auspices of the International Conference on Harmonization (ICH) of Technical Requirements for Registration of Pharmaceuticals for Human Use. The draft guideline recommends acceptable amounts of residual solvents in pharmaceuticals for the safety of the patient as well as recommending the use of less toxic solvents in the manufacture of drug substances and dosage forms. According to this guidelines, solvents are divided into three classes. These are:

Class 1: Solvents to be avoided. Known human carcinogens, strongly suspected human carcinogens, and environmental hazards.

Class 2: Solvents to be limited. Nongenotoxic animal carcinogens or possible causative agents of other irreversible toxicity such as neurotoxicity or teratogenicity; solvents suspected of other significant but reversible toxicities.

Class 3: Solvents with low toxic potential to man. No health based exposure limit is needed. Class 3 solvents have Permitted Daily Exposure (PDE) of 50 milligrams (mg) or more per day.

Ethanol and THF employed by the present invention are listed by the FDA in Class 3 and are therefore quite safe for commercial production of carotenoids for human use. The advantage of THF in compare to other organic solvents of Class 3 is due to the strong solubility of carotenoids in this solvent which allows the extraction of these pigments from the matrices of various plants in an efficient and speedy manner. In addition, THF is water soluble and therefore can be used in a homogenous phase extraction of carotenoids from plants in which significant amount of water may be present (Kale, Spinach, Collard green). The solubility strength of THF for carotenoids and the homogeneity of THF, ethanol, and water allow for the simultaneous extraction and saponification of carotenoids from plants. This is because the extracted carotenoids in a homogenous phase can be readily hydrolyzed at room temperature within several hours whereas in a heterogenous phase immiscible solvents such as a mixture of hexane, an alcohol, and water, would require high temperatures over extended period to accomplish the hydrolysis. The heterogeneous phase hydrolysis of carotenoids can present a serious problem especially in scaling up for commercial production. In such cases, the unavoidable high temperatures used for hydrolysis can increase the risk of oxidative degradation and isomerization of carotenoids.

In a typical process the Marigold meal (100 g), tetrahydrofuran (THF, 1000 ml), and sodium- or potassium hydroxide (25 g) in food grade ethanol (250 ml) are homogenized at room temperature. The homogenate is steeped at an elevated pH of about 11–14, preferably 12, for about two hours. Although food grade ethanol is preferred, other alcohols such as 1-butanol, 2-butanol, 2-methyl-1-propanol, 1-propanol, and 2-propanol which are all listed as safe in Class 3 solvents by the FDA may also be used. Preferred solvents are also selected for their boiling points. Solvents with boiling points of about 75° C. to 120° C. are preferred. Ethanol, with a boiling point of 78° C., is most preferred. The pH of the mixture is monitored and automatically maintained at about pH 12. An additional amount of sodium- or potassium hydroxide (25 g) in 250 ml of ethanol is normally needed to maintain the pH at 12. The extraction and saponification is completed in about 2 hours. The solvents are then evaporated and the residue is washed with 1000 ml of a 1/1 mixture water and alcohol to remove the base and the water soluble components. The lutein crystals are collected by centrifugation, washed with alcohol (100 ml), and dried under high vacuum overnight at room temperature. The lutein crystals (2.0 g) obtained are about 70% pure and can be recrystallized from a mixture of THF (20 ml) and water (30 ml) and dried under high vacuum overnight to give 1.2 g of lutein containing about 5% zeaxanthin in 97% purity.

Alternatively, the above 70% pure lutein can also be purified by passing a solution of this compound in THF/water (1.5/1.0) through a column of n-silica gel and subsequent of washing of the column with this solvent mixture. After collection of the lutein fraction, the THF is evaporated, the crystals of pure lutein are collected by centrifugation, and washed with 20 ml of an alcohol, preferably ethanol, to remove the residual water from the product. Drying under high vacuum gives 1.2 g of 97% pure lutein containing about 5% zeaxanthin. In another fraction from this purification, about 0.3 g of a mixture of lutein, anhydrolutein, alpha-cryptoxanthin, and beta-cryptoxanthin is also obtained.

When the simultaneous extraction and saponification process for isolation of lutein from Marigold was compared to a two-steps process, in which the plant was first extracted and then saponified; the results were identical.

The simultaneous extraction and saponification was also successfully applied to the isolation of 97% pure zeaxanthin (0.48 g) from LCM berries (455.5 g) and a mixture of lutein, beta-carotene, neoxanthin, violaxanthin, lutein epoxide (0.7 g) from Kale (1800 g).

SIMULTANEOUS EXTRACTION AND SAPONIFICATION

EXAMPLE 1

Isolation of Carotenoids from Marigolds

Marigold meal (100 g) was vigorously homogenized in a blender with tetrahydrofuran (THF, 1000 ml) and 10% ethanolic KOH (250 ml) at room temperature. The pH of the solution was kept at 12 by monitoring the extraction and hydrolysis with an automatic pH-meter. During the course of the extraction an additional 250 ml of 10% ethanolic KOH was needed to maintain the pH at 12. It is essential to avoid the addition of excessive amounts of the base to the mixture during the extraction and hydrolysis. This is because at a later purification step, the removal of the excess base will then require additional and un-necessary washing of the residue with large volumes of water which can be time consuming. The course of the extraction and hydrolysis was monitored by Thin Layer Chromatography (TLC) using hexane/acetone=90/10 on n-silica gel plates as well as by High Performance Liquid Chromatography (HPLC) according to a published procedure by the author (Khachik et al. J. Chrom. 449: 119–133, 1988). After 2 hours, carotenoid esters were shown to be completely hydrolyzed. The mixture was filtered off and the solids were washed with THF (1000 ml). The solvents were evaporated under reduced pressure at approximately 40° C. to almost dryness and the solids were stirred at room temperature with a 1/1 mixture of water and food grade ethanol (700 ml) for 10 minutes. The mixture was then centrifuged and the water/alcohol wash was removed. The washing of the solids was repeated 2 more times at which point all the base was shown to have been removed and the pH of the aqueous wash was at pH=7. The solids were washed with 100 ml of ethanol, centrifuged, and dried under high vacuum at room temperature overnight to give lutein as yellow crystals (2.0 g, 70% pure lutein). The HPLC analysis (Khachik et al. J. Chrom. Biomed. Appl. 582: 153–166, 1992) of the lutein crystals at this point revealed the carotenoid composition shown in Table I.

TABLE I

Carotenoid Composition of 70% Pure Lutein
Isolated from an Extract of Marigold Flowers

| Carotenoids | Composition (%) |
| --- | --- |
| all-E-Lutein | 93.0 |
| Total-Z-Luteins | 0.3 |
| all-E-Zeaxanthin | 5.4 |
| Anhydroluteins | 0.8 |
| alpha-Cryptoxanthin | 0.2 |
| beta-Cryptoxanthin | 0.3 |

Purification of Lutein by Recrystallization

The lutein crystals (2.0 g, 70% pure) were dissolved in THF (20 ml) and water (30 ml) was added to commence recrystallization. The mixture was stirred at room temperature for 10 minutes and the solids were separated by centrifugation. After removal of the solution, the lutein crystals were washed with ethanol (20 ml), centrifuged, and dried under high vacuum overnight at room temperature. This gave 1.2 g of lutein which was shown by HPLC-UV/Visible photodiode array detection coupled with Mass Spectrometry (MS) to be 97% pure but contained about 4% of all-E-zeaxanthin (Khachik et al. J. Chrom. Biomed. Appl. 582: 153–166, 1992).

The THF/water solution from the above recrystallization was evaporated to remove the THF and to precipitate small amounts of lutein along with other carotenoids (0.4 g) which were separated by centrifugation. The mixture of carotenoids were washed with small amounts of ethanol (about 4 ml) and dried under high vacuum. HPLC analysis of the dried solid showed that in addition to all-E-lutein, this fraction was enriched in 13,13'-di-Z-lutein (stereoisomer of lutein) as well as anhydrolutein, alpha-cryptoxanthin, and beta-cryptoxanthin.

Purification of Lutein and Other Carotenoids on a n-Silica Gel Column

The 70% pure lutein (2.0 g) was dissolved in THF (20 ml) and was passed through a glass column of n-Silica gel (15 cm L X 4 cm I.D.) packed under slight air pressure using THF/water (1.5/1.0). The column was washed with 200 ml of THF/water (1.5/1.0) and fractions 1 (50 ml) and 2 (150 ml) were collected. After evaporation of THF under reduced pressure at 40° C, and removal of water by centrifugation, fractions 1 and 2 were washed with 4 ml and 20 ml of ethanol, respectively, and dried under high vacuum at room temperature overnight. The first fraction (0.3 g) was shown by HPLC-UV/Vis-MS to be a mixture of anhydrolutein, alpha-cryptoxanthin, and beta-cryptoxanthin and the second fraction (1.2 g) was shown to be pure all-E-lutein (97%) but contained approximately 4% zeaxanthin.

EXAMPLE 2

Isolation of Carotenoids from Lycirm Chinese Mill (LCM BERRIES)

LCM berries (455.5 g) were rehydrated in a beaker containing 1000 ml of water overnight at room temperature. The water was decanted off and the LCM berries were vigorously homogenized with THF (2000 ml) and 10% ethanolic KOH (250 ml) at room temperature. The pH of the solution was maintained at 12 by monitoring the extraction and hydrolysis with an automatic pH-meter. During the course of the extraction an additional amount of 250 ml of 10% ethanolic KOH was needed to keep the pH at 12. The course of the extraction and hydrolysis was monitored by Thin Layer Chromatography (TLC) using hexane/acetone= 90/10 on n-silica gel plates as well as by High Performance Liquid Chromatography (HPLC) according to a published procedure by the author (Khachik et al. J. Chrom. 449: 119–133, 1988). After 2 hours, carotenoid esters were shown to be completely hydrolyzed. The mixture was filtered off and the solids were washed with THF (with about 500 ml). The solvents were evaporated under reduced pressure at approximately 40° C. to almost dryness and the solids were stirred at room temperature with a 1/1 mixture of water and food grade ethanol (about 100 ml) for about 10 minutes. The mixture was then centrifuged and the water/alcohol wash was removed. The washing of the solids was repeated 2 more times at which point all the base was shown to have been removed and the pH of the aqueous wash was at pH=7. The solids were washed with 30 ml of ethanol, centrifuged, and dried under high vacuum at room temperature overnight to give zeaxanthin as orange crystals (0.48 g, 75% pure zeaxanthin). The HPLC analysis (Khachik et al. J. Chrom. Biomed. Appl. 582: 153–166, 1992) of the zeaxanthin crystals at this point revealed the carotenoid composition shown in Table II.

TABLE II

Carotenoid Composition of 75% Pure Zeaxanthin Isolated from an Extract of Lycium Chinese Mill

| Carotenoids | Composition (%) |
|---|---|
| all-E-Zeaxanthin | 91.0 |
| Total-Z-Zeaxanthins | 5.8 |
| alpha-Cryptoxanthin | 1.1 |
| beta-Cryptoxanthin | 1.3 |
| beta-Carotene | 0.8 |

Purification of Zeaxanthin by Recrystallization

The zeaxanthin crystals (0.48 g, 75% pure) were dissolved in THF (5 ml) and water (about 10 ml) was added to commence recrystallization. The mixture was stirred at room temperature for about 10 minutes and the solids were separated by centrifugation. After removal of the solution, the zeaxanthin crystals were washed with ethanol (about 5 ml), centrifuged, and dried under high vacuum for about 8 hours at room temperature. This gave 0.35 g of zeaxanthin which was shown by HPLC-UV/Visible photodiode array detection coupled with Mass Spectrometry (MS) to be 97% pure but contained about 3.5% of Z-zeaxanthins (Khachik et al. J. Chrom. Biomed. Appl. 582: 153–166, 1992).

The THF/water solution from the above recrystallization was evaporated to remove the THF and to precipitate small amount of zeaxanthin along with other carotenoids (0.1 g) which were separated by centrifugation. The mixture of carotenoids were washed with small amount of ethanol (1 ml) and dried under high vacuum. HPLC analysis of the dried solid showed that in addition to zeaxanthin, this fraction was enriched in alpha-cryptoxanthin, beta-cryptoxanthin, and beta-carotene.

EXAMPLE 3

Isolation of Carotenoids from Greens

The general procedure described here for the isolation of carotenoids from Kale was similarly applied to spinach and collard green.

Fresh kale (1800 g) was placed in a Robot-que and cut into small peace. This was vigorously homogenized with THF (5000 ml) and 10% ethanolic KOH (500 ml) at room temperature. The pH of the solution was maintained at 12 by monitoring the extraction and hydrolysis with a pH-meter. During the course of the extraction an additional amount of 500 ml of 10% ethanolic KOH was needed to maintain the pH at 12. The course of the extraction and hydrolysis of chlorophylls to their derivatives was monitored by Thin Layer Chromatography (TLC) as well as by High Performance Liquid Chromatography (HPLC) according to a published procedure by the author (Khachik et al. J. Agric. Food Chem. 34:603–616, 1986). After 2 hours, chlorophylls were completely hydrolyzed to their water soluble derivatives. The mixture was filtered off and the solids were washed with THF (1000 ml). The solvents were evaporated under reduced pressure at approximately 40° C. to almost dryness and the solids were stirred at room temperature with a 1/1 mixture of water and food grade ethanol (100 ml) for 10 minutes. The mixture was then centrifuged and the water/alcohol wash was removed. The washing of the solids was repeated 4 more times at which point all the base and the green chlorophyll derivatives were removed and the pH of the aqueous wash was at pH=7. The solids were washed with 30 ml of ethanol, centrifuged, and dried under high vacuum at room temperature overnight to give a mixture of carotenoids (0.923 g). This was dissolved in 5 ml of THF and treated with 10 ml of water to recrystallize carotenoids which were separated by centrifugation. After removal of the solvents, the crystals were washed with ethanol (5 ml) and dried under high vacuum overnight at room temperature. The HPLC analysis (Khachik et al. J. Agric. Food Chem. 34: 603–616, 1986) of the mixture (0.7 g) revealed the carotenoid composition shown in Table III.

TABLE III

Carotenoid Composition of a Purified Extract from Kale

| Carotenoids | Composition (%) |
|---|---|
| all-E-Lutein | 48.7 |
| Total-Z-Luteins | 2.3 |
| beta-Carotene | 19.0 |
| Neoxanthin | 16.0 |

TABLE III-continued

| Carotenoid Composition of a Purified Extract from Kale | |
|---|---|
| Carotenoids | Composition (%) |
| Violaxanthin | 11.0 |
| Lutein Epoxide | 3.0 |

From the above examples it can be seen that the present invention has accomplished the isolation of lutein and zeaxanthin as well as a mixture of several rare carotenoids from plants in substantially pure form under controlled and mild condition to preserve the integrity of these essential dietary compounds. This economically viable process employs solvents which are not toxic and as a result, the carotenoids purified by this procedure can be safely used as nutritional supplements or food coloring additives.

What is claimed is:

1. A method for the extraction and saponification of lutein esters or zeaxanthin esters from a plant source containing lutein esters or zeaxanthin esters, comprising; extracting lutein esters or zeaxanthin esters from said plant source by contacting the plant source with a solution containing tetrahydrofuran and an alcohol to obtain a mixture; saponifying the mixture; removing the tetrahydrofuran and alcohol from the mixture to obtain a residue; washing the residue with an aqueous solution; and isolating lutein or zeaxanthin as crystals.

2. The method of claim 1 wherein extraction and saponification are conducted simultaneously.

3. The method of claim 1 wherein the alcohol is selected form the group consisting of ethanol, 1-butanol, 2-butanol, 2-methyl-1-propanol, 1-propanol, and 2-propanol.

4. The method of claim 3 wherein the alcohol is ethanol.

5. A method for the simultaneous extraction and hydrolysis of lutein esters from marigold petals, comprising: extracting and saponifying lutein esters from said petals by contacting said petals with a solution comprising tetrahydrofuran and an alcohol at an elevated pH to obtain a mixture comprising hydrolyzed lutein; removing unwanted solids from the mixture to obtain a liquids portion; removing the tetrahydrofuran and alcohol from the liquids portion to obtain a residue comprising lutein free from esters; washing the residue with an aqueous mixture; and collecting lutein crystals.

6. The method of claim 5 wherein the alcohol is selected form the group consisting of ethanol, 1-butanol, 2-butanol, 2-methyl-1-propanol, 1-propanol, and 2-propanol.

7. The method of claim 5 further comprising washing the collected lutein crystals with an alcohol having a boiling point between 75° C. and 120° C., and drying the crystals.

8. The method of claim 7 further comprising recrystalizing the lutein crystals from an aqueous mixture of tetrahydrofuran.

9. The method of claim 5 wherein the pH is monitored during the simultaneous extracting and saponifying steps and the pH is adjusted by adding base.

10. The method of claim 5 wherein saponification (hydrolysis) occurs during the extraction step and the base is NaOH or KOH.

11. The method of claim 5 wherein the marigold petals, prior to extraction, are milled to a meal.

12. The method of claim 5 wherein the pH is about 12.

13. The method of claim 1 wherein the extracting and saponifying steps are conducted at about room temperature in two hours.

14. A method for the simultaneous extraction of lutein and conversion of chlorophylls to water soluable derivitives present in green leafy vegetables, comprising: extracting lutein and hydrolyizing chlorophylls from said vegetables by contacting said vegetables with a solution comprising tetrahydrofuran and an alcohol at an elevated pH to obtain a mixture; removing solids from the mixture to obtain a liquid extract; removing the tetrahydrofuran and alcohol from the liquid extract to obtain a residue; washing the residue with an aqueous mixture to remove the base and water soluble chlorophyll derivatives; and collecting lutein.

15. The method of claim 2 wherein the plant source is Lycium Chinese berries or marigold petals or green leafy vegetables.

16. A method for the simultaneous extraction and saponification of one or more carotenoids from a plant source comprising: steeping the plant source in the presence of only class 3 solvents, at room temperature, to obtain an extract comprising carotenoid extraction products.

17. The method of claim 16 wherein solvents for extraction and saponification are tetrahydrofuran, and an alcohol selected from the group consisting of ethanol, 1-butanol, 2-butanol, 2-methyl-1-propanol, 1-propanol, and 2-proponol.

18. The method of claim 16 wherein the solvent is a mixture of tetrahydrofuran and ethanol, and extraction/saponification is conducted in the presence of KOH.

19. The method of claim 16 wherein the extraction/saponification is conducted at a pH of about 12.

20. The method of claim 18 wherein the extraction/saponification is conducted at room temperature for two hours.

21. The method of claim 1 further comprising purifying crystals by dissolving the crystals to create a solution and passing the solution of lutein or zeaxanthin through a column packed with n-silica gel and isolating pure lutein or zeaxanthin.

22. A method for isolating lutein comprising simultaneously extracting and saponifying lutein esters.

* * * * *